US010952905B2

(12) United States Patent
Fritz et al.

(10) Patent No.: US 10,952,905 B2
(45) Date of Patent: Mar. 23, 2021

(54) ABSORBENT CORES AND APPARATUS AND METHODS FOR PRODUCING ABSORBENT CORES

(71) Applicant: Curt G. Joa, Inc., Sheboygan Falls, WI (US)

(72) Inventors: Jeffrey W. Fritz, Plymouth, WI (US); Gottfried Jason Hohm, Sheboygan Falls, WI (US); Cory Veldman, Plymouth, WI (US); Daniel A. Peterson, Sheboygan, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 172 days.

(21) Appl. No.: 15/949,258

(22) Filed: Apr. 10, 2018

(65) Prior Publication Data

US 2018/0296398 A1  Oct. 18, 2018

Related U.S. Application Data

(60) Provisional application No. 62/485,080, filed on Apr. 13, 2017.

(51) Int. Cl.
| | |
|---|---|
| *A61F 13/15* | (2006.01) |
| *B29C 65/74* | (2006.01) |
| *A61F 13/531* | (2006.01) |
| *B29C 65/00* | (2006.01) |
| *A61F 13/53* | (2006.01) |
| *B29L 31/48* | (2006.01) |

(52) U.S. Cl.
CPC .. *A61F 13/15658* (2013.01); *A61F 13/15601* (2013.01); *A61F 13/15723* (2013.01); *A61F 13/15739* (2013.01); *A61F 13/15804* (2013.01); *A61F 13/531* (2013.01); *B29C 65/74* (2013.01); *B29C 66/72523* (2013.01); *A61F 2013/15926* (2013.01); *A61F 2013/530481* (2013.01); *B29K 2995/0046* (2013.01); *B29L 2031/4878* (2013.01)

(58) Field of Classification Search
CPC .......... A61F 13/15658; A61F 13/15804; A61F 13/15739
See application file for complete search history.

(56) References Cited

U.S. PATENT DOCUMENTS

| | | | |
|---|---|---|---|
| 2008/0312628 A1* | 12/2008 | Hundorf | A61F 13/5323 604/378 |
| 2014/0276508 A1* | 9/2014 | Wright | A61F 13/539 604/365 |
| 2016/0030258 A1* | 2/2016 | Wei | A61F 13/5323 604/384 |

* cited by examiner

*Primary Examiner* — Christopher T Schatz
(74) *Attorney, Agent, or Firm* — Ziolkowski Patent Solutions Group, SC

(57) ABSTRACT

A pulpless core is provided with flexibility for superabsorbent expansion by using elastic strands stretched and coupled to a nonwoven layer, and then relaxed partially to create receiving valleys (puckers) and the puckers are provided with superabsorbent polymer, and then a layer of nonwoven or acquisition film can be coupled on top of nonwoven/elastic/sap carrier layers to create an absorbent core laminate. A tubular core can be created and placed into a product with or without additional absorbent material between adjacent tubular members. A printed back sheet corresponding to either the tubular core shape, or void spaces between tubular members can be provide. A forming drum pocket can be profiled to match tube or tube shaped zones and elastic placements between adjacent tubes, if desired.

9 Claims, 12 Drawing Sheets

ABSORBENT CORES AND APPARATUS AND METHODS FOR PRODUCING ABSORBENT CORES

RELATED APPLICATION

This application claims the benefit of U.S. Provisional Patent Application Ser. No. 62/485,080, filed 13 Apr. 2017.

BACKGROUND OF THE INVENTION

This invention relates to formation of pulpless absorbent cores for use in disposable products such as diapers and sanitary napkins.

Sanitary napkins used in feminine hygiene are absorbent items worn by women to recover undesirable bodily discharges. These absorbent articles are typically comprised of an absorbent core sandwiched between layers of woven or non-woven materials.

Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in assembly line fashion.

In the creation of a diaper (and, oftentimes also in conjunction with feminine hygiene products), multiple roll-fed web processes are typically utilized.

To create an absorbent insert, the cellulose pulp is unwound from the provided raw material roll and pulverized by a pulp mill. Discrete pulp cores are formed by a core forming assembly and placed on a continuous tissue web. Optionally, superabsorbent powder or polymer (SAP) may be added to the pulp core. The tissue web is wrapped around the pulp core. The wrapped core is debulked by proceeding through a calendar unit, which at least partially compresses the core, thereby increasing its density and structural integrity. After debulking, the tissue-wrapped core is passed through a segregation or knife unit, where individual wrapped cores are cut. The cut cores are conveyed, at the proper pitch, or spacing, to a boundary compression unit.

While the insert cores are being formed, other insert components are being prepared to be presented to the boundary compression unit. For instance, the poly sheet is prepared to receive a cut core. Like the cellulose pulp, poly sheet material is usually provided in roll form. They poly sheet is fed through a splicer and accumulator, coated with an adhesive in a predetermined pattern, and then presented to the boundary compression unit. In addition to the poly sheet, which may form the bottom of the insert, a two-ply top sheet may also be formed in parallel to the core formation. Representative plies are an acquisition web material and a nonwoven web material, both of which are fed from material rolls, through a splicer and accumulators. The plies are coated with adhesive, adhered together, cut to size, and presented to the boundary compression unit. Therefore, at the boundary compression unit, three components are provided for assembly: the poly bottom sheet, the core, and the two-ply top sheet.

A representative boundary compression unit includes a die roller and a platen roller. When all three insert components are provided to the boundary compression unit, the nip of the rollers properly compresses the boundary of the insert. Thus, provided at the output of the boundary compression unit is a string of interconnected diaper inserts. The diaper inserts are then separated by an insert knife assembly and properly oriented. At this point, the completed insert is ready for placement on a diaper chassis.

A representative diaper chassis comprises nonwoven web material and support structure. The diaper support structure is generally elastic and may include leg elastic, waistband elastic and belly band elastic. The support structure is usually sandwiched between layers of the nonwoven web material, which is fed from material rolls, through splicers and accumulators. The chassis may also be provided with several patches, besides the absorbent insert. Representative patches include adhesive tape tabs and resealable closures.

The process utilizes two main carrier webs; a nonwoven web which forms an inner liner web, and an outer web that forms an outwardly facing layer in the finished diaper. In a representative chassis process, the nonwoven web is slit at a slitter station by rotary knives along three lines, thereby forming four webs. One of the lines is on approximately the centerline of the web and the other two lines are parallel to and spaced a short distance from the centerline. The effect of such slicing is twofold; first, to separate the nonwoven web into two inner diaper liners. One liner will become the inside of the front of the diaper, and the second liner will become the inside of the back of that garment. Second, two separate, relatively narrow strips are formed that may be subsequently used to cover and entrap portions of the leg-hole elastics. The strips can be separated physically by an angularly disposed spreader roll and aligned laterally with their downstream target positions on the inner edges of the formed liners.

After the nonwoven web is sliced, an adhesive is applied to the liners in a predetermined pattern in preparation to receive leg-hole elastic. The leg-hole elastic is applied to the liners and then covered with the narrow strips previously separated from the nonwoven web. Adhesive is applied to the outer web, which is then combined with the assembled inner webs having elastic thereon, thereby forming the diaper chassis. Next, after the elastic members have been sandwiched between the inner and outer webs, an adhesive is applied to the chassis. The chassis is now ready to receive an insert.

To assemble the final diaper product, the insert must be combined with the chassis. The placement of the insert onto the chassis occurs on a placement drum or at a patch applicator. The inserts are provided to the chassis on the placement drum at a desired pitch or spacing. The generally flat chassis/insert combination is then folded so that the inner webs face each other, and the combination is trimmed. A sealer bonds the webs at appropriate locations prior to individual diapers being cut from the folded and sealed webs.

Generally, disposable undergarments such as pants-type diapers are made up of two nonwoven layers of material with elastic strands of material placed between the two nonwoven layers of material thus creating an elastic web laminate. The layers of material are continuous sheets of material that are eventually cut into individual undergarment lengths. The elastic strands may be arranged and cut so that specific areas of the undergarment are free of elastic tension or forces. An absorbent pad, often contained within an insert or core is then also placed into the pants-type diaper product.

To insure the pants-type diaper retains a proper shape and to hold all of the added layers of the diaper, reinforcing layers and backing materials are normally added to the continuous sheets of material, with the reinforcing layers corresponding to the cut elastic strands of each individual blank. Each of these layers needs to be adhesively joined at some point in the manufacturing process to the elastic web laminate to form the completed undergarment.

Often, void spaces need to be created in the diaper, such as holes cut out of the main web for provided leg holes when the undergarment ultimately formed. To create the void spaces, the web is ordinarily die cut, with the web severed between a die and an anvil. The portion of the web material that is removed is referred to as a "chip." As the die wears throughout time, the severing of the chip from the web material becomes gradually a duller cut. This complicates the removal of the chip because the severing might not create a continuous cut out chip, with possibly some strands of the web material still coupling the chip with the web. It is desired to lengthen the amount of time and increase the number of chips that a single the can effectively be used for, to reduce the number of die change-outs.

Typically, the absorbent fibrous material is composed of cellulose wadding or cellulosic wood pulp material commonly referred to as "fluff", although a mixture of natural and synthetic fibers is within the scope of the invention. An absorbent core composed of wood pulp fluff is typically formed by employing conventional air laying techniques.

These absorbent cores have had their total absorbency improved greatly by the addition of superabsorbent material, or superabsorbent polymer (SAP) to the commonly used absorbent fibrous materials.

The ability of these absorbent cores to manage the typical surges of liquid flow is heavily dependent on the proper distribution of superabsorbent material within the absorbent fluff. When most superabsorbent materials absorb aqueous fluids, they swell substantially, often to double their dry dimensions or more at saturation. As these superabsorbent materials absorb fluid and swell, they generally become a gelatinous mass.

There has been a trend in reducing the bulk of diapers, in attempts to make them more like underwear and to take up less shelf space in retailer's outlets. Generally, the thinner the diaper, the higher the concentration of superabsorbent material required to produce the same level of absorbency. High levels of superabsorbent material, however, tend to be more difficult to control and to maintain in position.

In conventional core forming processes, three-dimensional fluff receiving pockets rotate about a vacuum drum. The pockets typically include baffles and screens which permit airflow through the pockets. The fluff is applied to the fluff receiving pockets entrained in air applied to the pockets. The vacuum attracts the fluff to a screen-like mesh that forms the pockets. The fluff is retained by the pockets, and the amount of fluff builds up from the screen forming the pocket. However, some fluff passes through the screen of the pockets and into the vacuum stream that is drawing the fluff into the pocket. Thus, some fluff undesirably becomes entrained in the vacuum stream.

In conventional core forming process, it is desired to balance the amount of air urging the fluff towards the core forming pocket and the amount of vacuum used to retain the fluff within the pocket. Machine processes have become more complex as speeds of machines have increased, so air handling systems used in this process have greater demands placed on them. For instance, if the machine is running faster, pulp is required to be delivered to the core forming pocket quicker, necessitating a greater air flow to the pocket. To deliver more pulp to the pocket, more vacuum is required to retain the pulp within the pocket. One complication is in achieving optimum balance between air in to the pocket and vacuum applied to the back side of the pocket.

Imbalance between the amount of air supplying pulp to the core forming pocket and vacuum applied to the back of the pocket, holding the fluff in, causes puffs of fluff to escape forming chamber. Conventional core forming technology allows for limited adjustability to try and achieve the optimum balance between air in and vacuum. The largest air delivery is from fiberizing mill which supplies fluff and blows the fluff into the core forming chamber.

Another source of air into forming process is from the dust collection equipment, which returns collected fluff from the vacuum stream to the core forming drum. Beginning with fluff that passes through the core forming pocket, the vacuum stream leads the fluff within the vacuum stream to the dust collection unit. A filter within the dust collection unit captures this fluff, this fluff is removed from the filter, and recirculated into the core forming process. Typically, this vacuum stream is fed into a drum filter housing, such as described in U.S. Pat. No. 5,679,136, commercial embodiments of which are available from the Osprey Corporation, and which is incorporated herein by reference.

Pulpless cores are a recent development. In these embodiments, an absorbent core is formed without cellulosic fibers. It is known to use SAP with pockets created in a substrate (sometimes with vacuum), but formed pockets resist expansion with SAP expansion.

SUMMARY OF THE INVENTION

This invention relates to a method and apparatus for forming an absorbent core or cores. More particularly, the cores of the present invention, and methods for forming them, reduce or eliminate the absorbent fibrous material composed of cellulose wadding or cellulosic wood pulp material. The result is a pulpless core.

The present invention allows the ability to extend in a channel created along the machine direction if desired. Once the SAP expands, the corrugations (rugosity) can be elongated out, and wasted SAP is avoided if the SAP not exposed to liquid. Wasted SAP can be also avoided by a better control of SAP delivery, such as gradient deposition or pattern deposition. In the current art the acquisition/distribution layer (ADL) is responsible for all the liquid distribution, but in the present invention, the core itself can assist with even liquid retention, acquisition and distribution to the core.

A core is provided with flexibility for superabsorbent expansion by using elastic strands stretched and coupled to a preferably nonwoven layer, using elastic adhesive for example, and then the elastic/nonwoven combination is relaxed partially to still create receiving valleys (puckers) and these are filled with SAP and then a layer of nonwoven or acquisition film can be added on top of the elastic/nonwoven combination carrying SAP. The top nonwoven can be coupled to the elastic/nonwoven combination for instance by glue with core integrity adhesive.

In the present invention, the core preferably has some stretch in either the machine or cross-machine direction, which can assist with the fit of the product. Inextensible cores do not stretch, but the present invention provides for controlled amount and directional stretch as desired. The amount of stretch is fully adjustable by how much the elastic strands are initially stretched prior to coupling with a non-woven layer, and by how much the elastic/non-woven combination is relaxed. Additionally, directional stretch or patterned stretch can be provided by changing the elastic laydown pattern.

An absorbent core material is disclosed comprising a first material layer; a series of elongated elastic strand members running in a machine direction and spaced apart in a cross machine direction, said elongated elastic members coupled to said first material layer at a first tension of said elongated elastic strand members; a superabsorbent polymer material provided in gaps between adjacent elongated elastic members at a second tension of said elongated elastic strand members, said first tension greater than said second tension; a second material layer coupled to said elongated elastic members; said first material layer, said elastic members, said superabsorbent polymer and said second material layer creating a stretchable absorbent core web. The de-tensioning of the elastic creates valleys or depressions in the first material layer which can capture the superabsorbent material, and when the second material layer is provided and coupled to the first material layer, the stretchable absorbent core web is formed. A first zone comprising said first material layer, said elastic members, said superabsorbent polymer and said second material layer is disclosed; and a second zone comprising said first material layer coupled directly to said second material layer, said second zone substantially free of superabsorbent polymer is disclosed. After formation of the stretchable absorbent core web, the stretchable absorbent core web can be severed into discrete core portions, and placed onto a diaper chassis, or incorporated into a diaper product or a different type of absorbent disposable product as desired. The superabsorbent polymer material can provided intermittently in said machine direction to create a machine direction superabsorbent polymer gap, and at this gap can be where said absorbent core material is severed into discrete core portions.

A tubular core can be created and placed into a product with or without additional absorbent material between adjacent tubular members. A printed back sheet corresponding to either the tubular core shape, or void spaces between tubular members can be provide. A forming drum pocket can be profiled to match tube or tube shaped zones and elastic placements between adjacent tubes, if desired. Disclosed also is a method of forming separate core elements (wrapped), perhaps even on separate forming drums, and then combining the individual wrapped core elements between two webs where the webs are pressed together to form web-to-web bonds between the core elements. This would create continuous void channels (completely free of fluff and/or SAP) between core elements. Unlike the prior art where the channels (regardless of shape) form "islands" in the midst of an individual core assembly. Individual core strips can be formed in series, or made independently from one another. One or more forming units if necessary can be used for core formation. Core strips can be formed continuously, or discrete.

A tubular core can be created and placed into a product with or without additional absorbent material between adjacent tubular members. A printed back sheet corresponding to either the tubular core shape, or void spaces between tubular members can be provide. A forming drum pocket can be profiled to match tube or tube shaped zones and elastic placements between adjacent tubes, if desired.

A method of forming a disposable product is disclosed comprising providing a base layer; providing a series of tubular absorbent core members of absorbent material carried by said base layer; providing a topsheet; and coupling said topsheet to said base layer between adjacent tubular absorbent core members to create a continuous comps web of absorbent core material. In a preferred embodiment, said tubular absorbent core members are provided parallel to one another. In one embodiment, an elastic strand is carried between said base layer and said topsheet, said elastic strand provided between adjacent tubular absorbent core members.

In another embodiment, said tubular absorbent core members are formed on a rotating vacuum drum, said rotating vacuum drum having pockets shaped to carry a predetermined amount of absorbent material, with the absorbent material being superabsorbent polymer or fluff material, or a combination of both. If desired, the tubular core members can be provided with a nonwoven wrap encapsulating absorbent material, prior to said step of providing said series of tubular absorbent core members of absorbent material carried by said base layer. If desired, the tubular core members can be end sealed in a machine direction at a first and a second end of said tubular core members. Also, the method can further comprise either continuously or intermittently bonding said base layer and said top layer between adjacent tubular core members.

Prior to introduction into a final product, the continuous composite web can be severed into discrete cores.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention.

In a preferred embodiment, creation of an absorbent core is accomplished by using two layers of nonwoven material 12 and 20, sandwiching SAP 16 and elastic strands 14 between the two layers of nonwoven material 12 and 20. However, in place of one or both of the nonwoven material layers 12 and 20, other materials can be used, such as woven materials, elastic materials, or any other useful material. The invention is not limited to use of nonwoven material layers in creating the laminate.

Figure 1A:
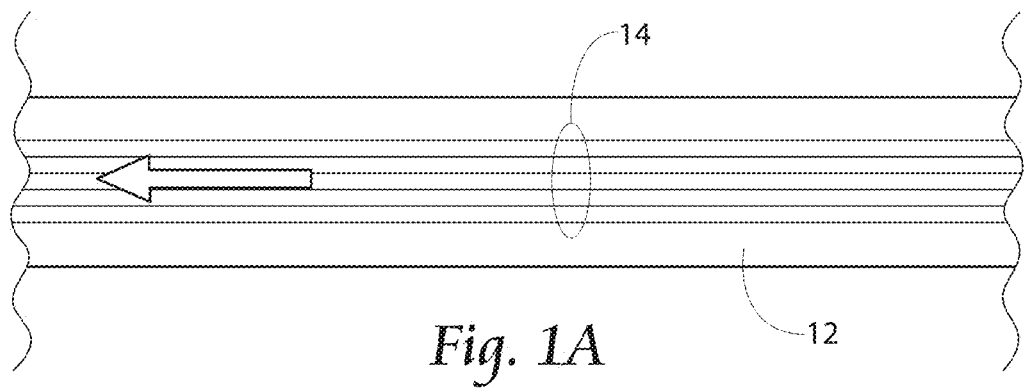
FIGS. 1A and 1B are in process top and side views respectively, of a core forming process of the present invention, with a first nonwoven web receiving a plurality of elastic strands under tension.
Figure 1B:
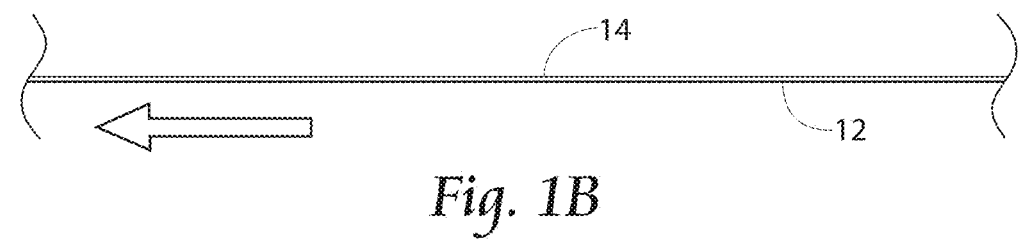

Referring now to FIGS. 1A and 1B, in process top and side views respectively, of a core forming process of the present invention are shown. A first nonwoven web 12 receives a plurality of elastic strands 14 under tension.

Figure 2A:
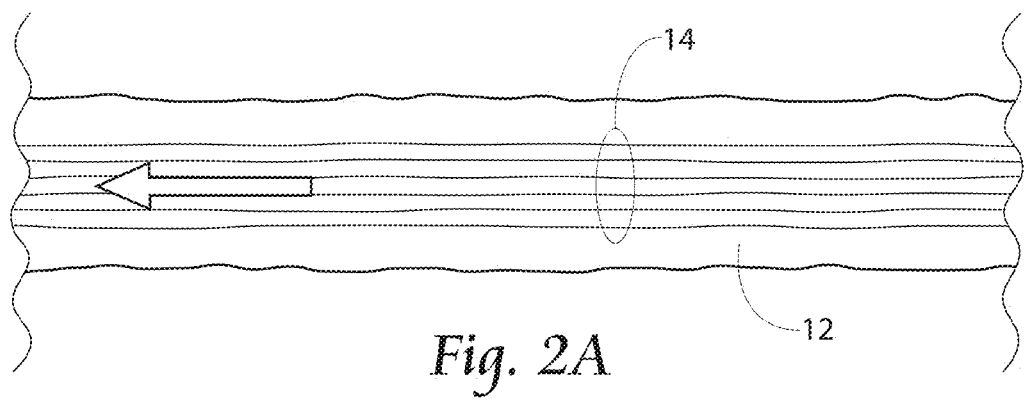
FIGS. 2A and 2B are in process top and side views respectively, showing a first tension let off of the elastic strands, to create peaks and valleys in the nonwoven.
Figure 2B:
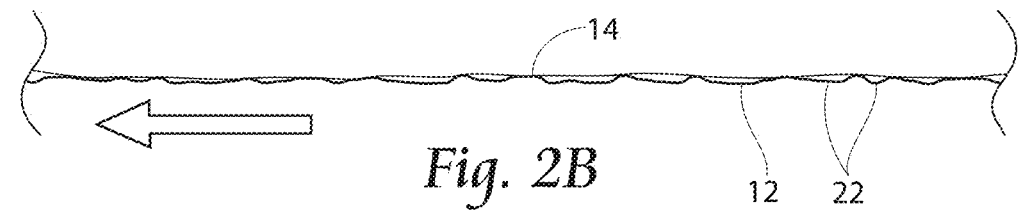
Figure 3A:
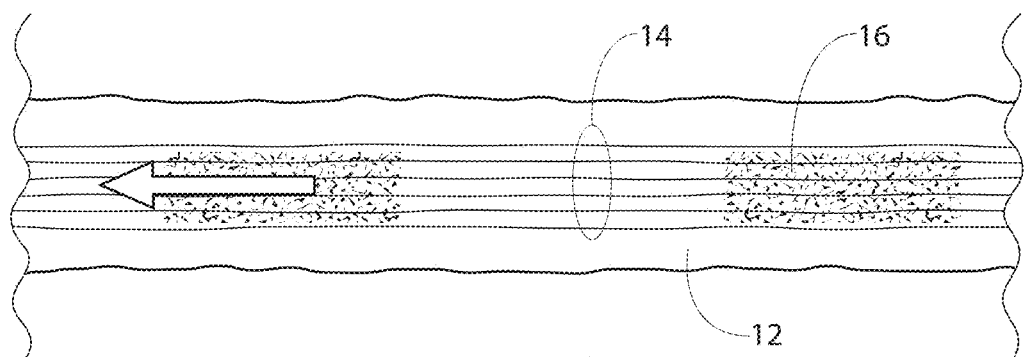
FIGS. 3A and 3B are in process top and side views respectively, showing a SAP distribution system applying SAP laid into the created peaks and valleys in the nonwoven.
Figure 3B:
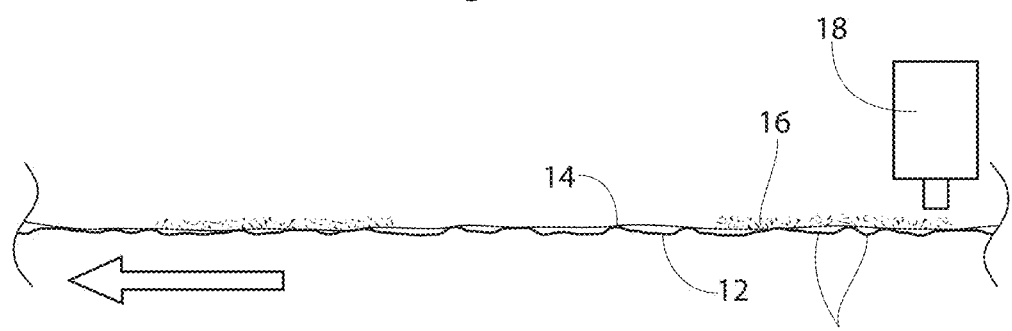

Referring now to FIGS. 2A and 2B, a first tension let off of the elastic strands 14 is allowed, to create peaks and valleys (or puckers) 22 in the nonwoven 12. Referring now to FIGS. 3A and 3B, a SAP distribution system 19 applies SAP laid 16 into the created peaks and valleys 22 in the nonwoven 12. The created peaks and valleys 22 act as pockets to carry the SAP 16. SAP 16 can be laid continuously (not shown) or discontinuously as shown. The SAP 16 delivery methods can be vibratory, by dimple drum, timed delivery, or any other methods known in the art. Additionally, the coordination between the SAP 16 deposition and the timing and orientation of joining nonwoven layer 20 can vary between in a vertical SAP 16 drop into a gap between vertically running web 20 and combined web 12/16 through nips, or the SAP 16 can be deposited onto horizontally machine direction running web 12/16 so that the pockets 22 can be collecting SAP 16 prior to horizontal machine direction running web 20.

The dimensions of the puckers 22 are adjustable with different spacing or number of strands of elastic 14. It may be desirable to vary the spacing and pucker size to allow higher or lower concentrations of SAP 16 in some sections of the diaper. The level of stretch in the strands 14 and the amount of relaxation before SAP 16 deposition can also change the pucker 22 dimensions.

In a preferred embodiment, SAP 16 can be deposited on nonwoven layer 12 while web 12 is moving horizontally in the machine direction, and when the second nonwoven layer 20 is applied and coupled, the combined pulpless core web can move downstream in any desired fashion.

Figure 4A:
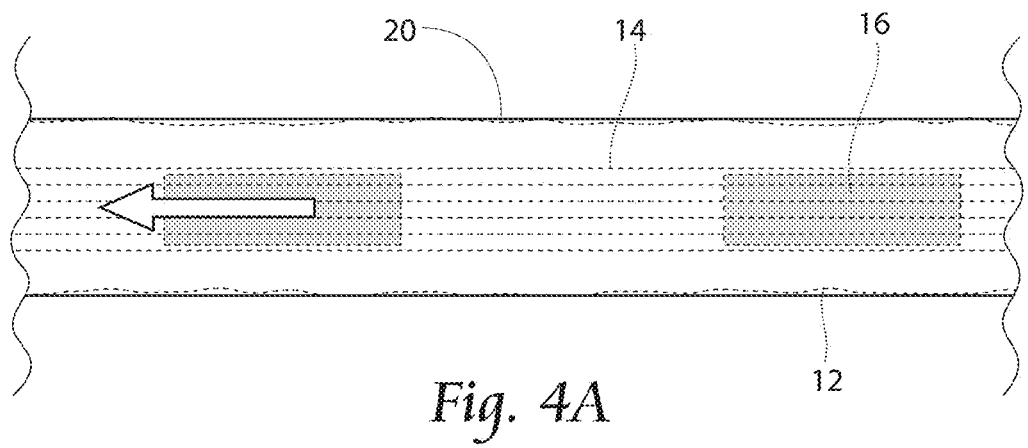
FIGS. 4A and 4B are in process top and side views respectively, showing a second nonwoven layer applied over the elastic strands and SAP filled peaks and valleys in the first nonwoven layer.
Figure 4B:
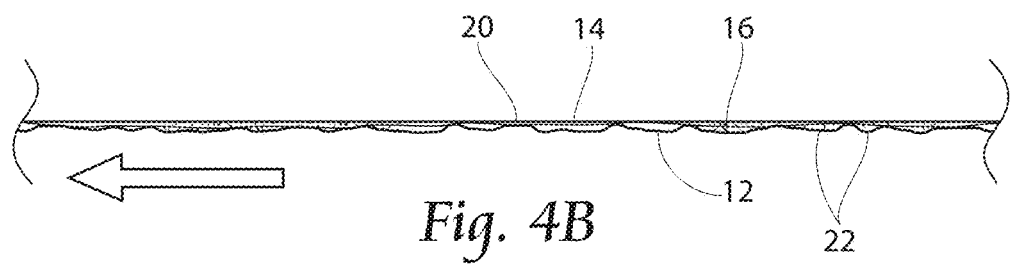
Figure 5:
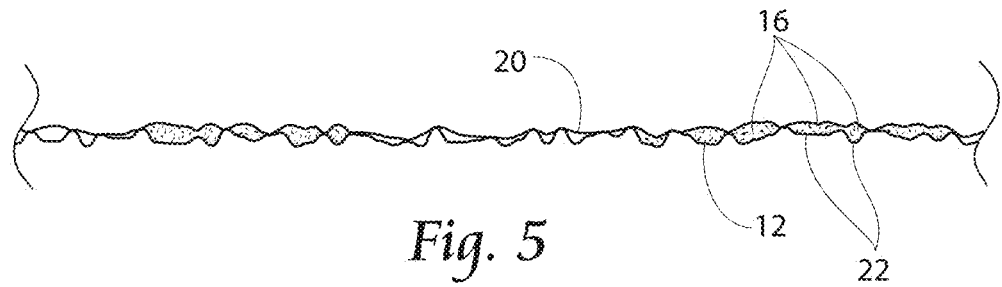
FIG. 5 is a side view of the second nonwoven layer applied over the elastic strands and SAP filled peaks and valleys in the first nonwoven layer, showing a second tension let off of the elastic strands to create a continuous web of absorbent core material.
Figure 9:
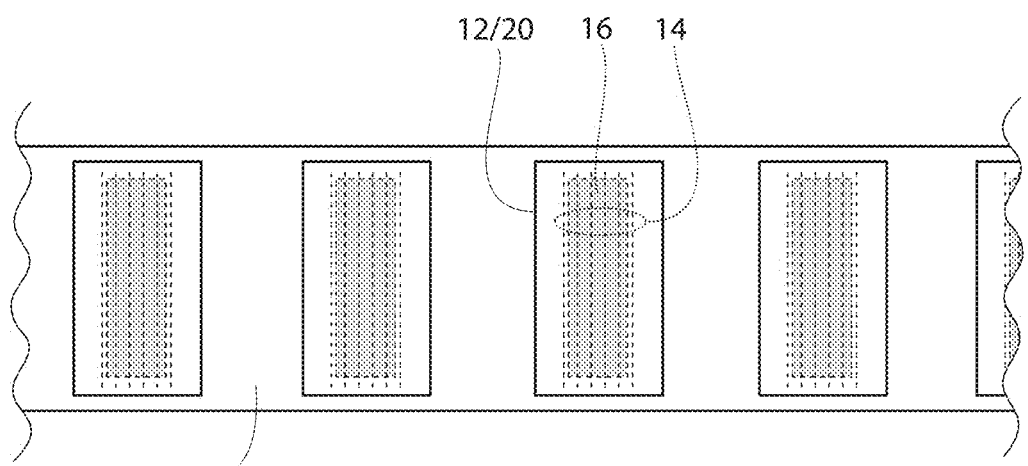
FIG. 9 is a top view of the second nonwoven layer applied over the elastic strands and SAP filled peaks and valleys in the first nonwoven layer, showing a second tension let off of the elastic strands to create a continuous web of absorbent core material, the absorbent core rotated and placed on a receiver running web.

Referring to FIGS. 4A and 4B, a second nonwoven 20 layer is applied over the elastic strands 14 and SAP 16 filled peaks and valleys 22 in the first nonwoven layer 12. As shown in FIG. 5, an alternate second tension let off of the elastic strands 14 create a continuous web of absorbent core material. The continuous web of absorbent core can then be processed as desired, for instance cut and placed onto a diaper chassis as individual cores, or rotated cut and placed as shown in FIG. 9 onto a running carrier web 24 which itself can be further processed as desired. The second nonwoven layer 20 could alternatively be a layer of acquisition/distribution film (an ADL layer). Describing an intended diaper from the outside, one preferred embodiment is a nonwoven layer, a poly layer, a nonwoven with lycra (core wrap) layer, SAP, an additional nonwoven (top core wrap), an acquisition/distribution layer, and a topsheet layer.

Referring still to FIGS. 4A and 4B, SAP is shown deposited in areas where the elastic strands 14 reside, but outer channels of elastics 14 can be created that either do or do not contain SAP 16, as desired.

Figure 6:
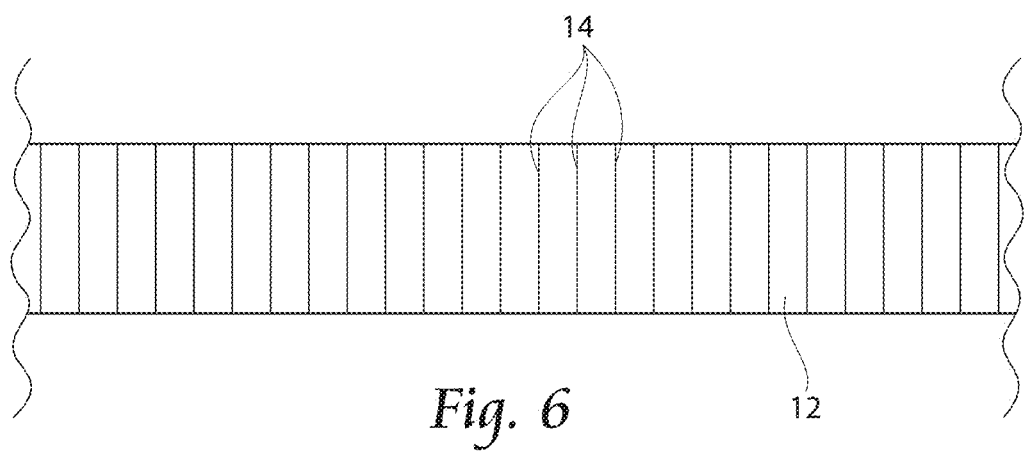
FIG. 6 is a first alternate embodiment of an elastic strand deposition pattern onto the first nonwoven layer.
Figure 7:
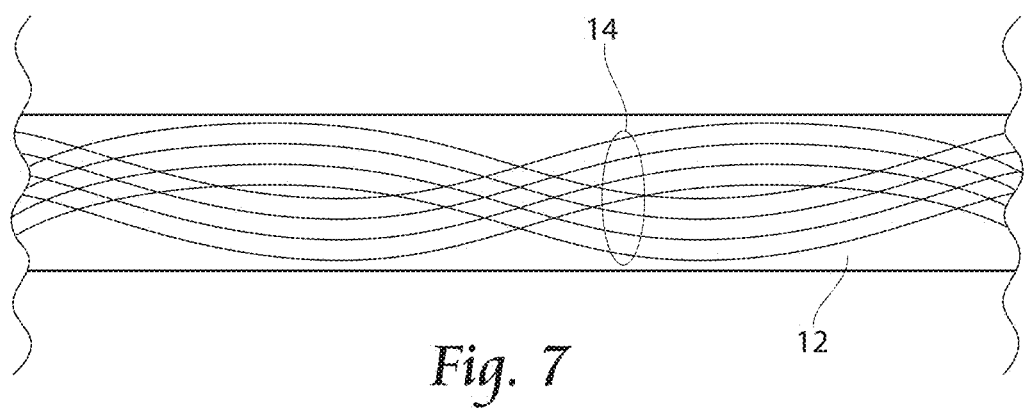
FIG. 7 is a second alternate embodiment of an elastic strand deposition pattern onto the first nonwoven layer.

FIGS. 6 and 7 show first and second alternate embodiments of elastic strand 14 deposition patterns onto the first nonwoven layer 12. In FIG. 6, the deposition is in the cross machine direction, and in FIG. 7, the deposition is in a curved fashion generally in the machine direction. The elastics 14 can be curved using curved or flared elastic deposition patterns as a method of tuning the absorption performance, and also to improve the fit and appearance of the final diaper product. The elastic deposition also provides control over the direction of elasticity of the core.

Figure 8:
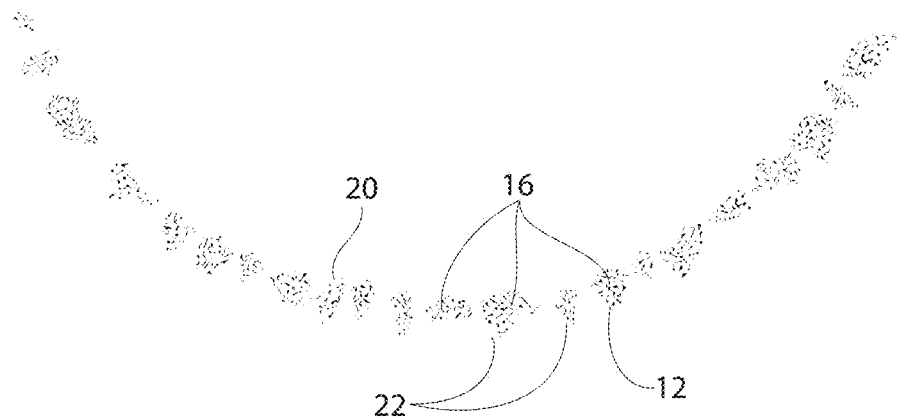
FIG. 8 is a cross sectional view of the second nonwoven layer applied over the elastic strands and SAP filled peaks and valleys in the first nonwoven layer, showing a second tension let off of the elastic strands, in an in use condition, for instance shaped as an absorbent core would be when a diaper is worn by a user.

Referring to FIG. 8, a cross sectional view of the second nonwoven 20 layer applied over the elastic strands 14 and SAP 16 filled peaks and valleys 22 in the first nonwoven layer 12, shows a second tension let off of the elastic strands 14, in an in use condition, for instance shaped as an absorbent core would be when a diaper is worn by a user. It is evident that the rugosities of the present invention desirably inhibit migration of SAP, for instance used beneficially in adult incontinent products. This feature could also increase the soft feel of the product, but in the current art, a thick ADL is needed to provide the soft feature of the product. The peaks and valleys or pockets 22 formed by the present invention minimized the tendency for the SAP 16 to accumulate through gravity to crotch area, the lowest portion of the core as shown. The elastic strands and its lamination with nonwoven in the middle of the core can better immobilize the SAP on its wet stage.

The present invention may permit lower performance, less expensive, elastics to be used because the elastics and the cores formed thereby can hold a shape at body temperature. Less costly variations become possible e.g. lower decitex Spandex, plastomers or high copolymer olefins that are semi elastic. In place of or in addition to traditional elastics 14 as shown, ribbons, or films slit into ribbons or ribbon like elements can be used in order to access these less costly technologies. The present invention can also use ultrasonic bonding to couple the layers (selecting Polypropylene as a blend component for example), or ultrasonic bonding can be used to trap elastic strands.

The entire crotch area can be provided with elasticity, and when combined with a front and back stretch panel, results in an overall diaper product which provides elastic from end to end of the diaper product if desired.

An additional embodiment (not shown), is that several layers of the absorbent core can be used. For instance, each layer might be designed for a different level of absorbency, or have different directional zones in it.

Additionally, a leg cuff could be built with into the core concept by stretching the outer strands of elastics 14 to a higher draw ratio than the central strands 14, and then when the product is allowed to spring back these strands of Lycra will raise up to make a bowl or boat shape without requiring a special apparatus and additional materials.

Figure 10:
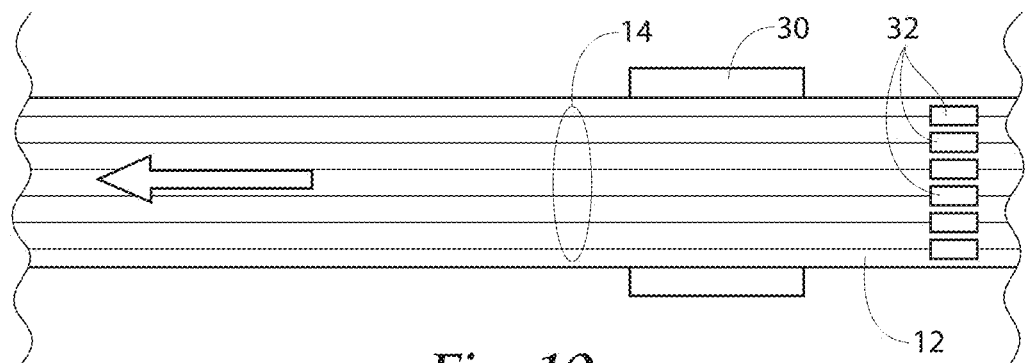
FIG. 10 is a top view of a portion of a system for producing an absorbent core.
Figure 11:
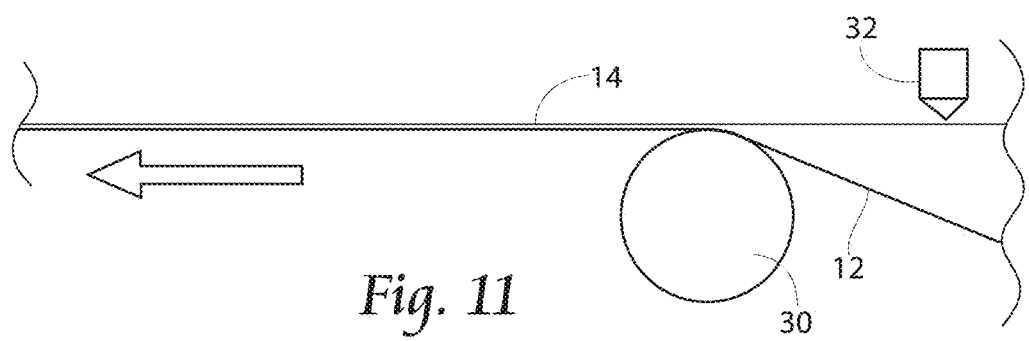
FIG. 11 is a side view of the portion of the system shown in FIG. 10.

Referring now to FIG. 10, a top view (and in FIG. 11, a side view) of a portion of a system for producing an absorbent core laminate 12/14/16/20 is shown. Adhesive applicator or applicators 32 apply adhesive preferably to elastic strands 14 (or to nonwoven layer 12) and adhesive strands 14 are brought into contact with nonwoven layer 12 by passing the strands 14 and nonwoven layer 12 over a roller 30. Alternatively (not shown), a thermally compatible elastic 14 in strand or ribbon form can be used and ultrasonically bonded where desired.

Figure 12:
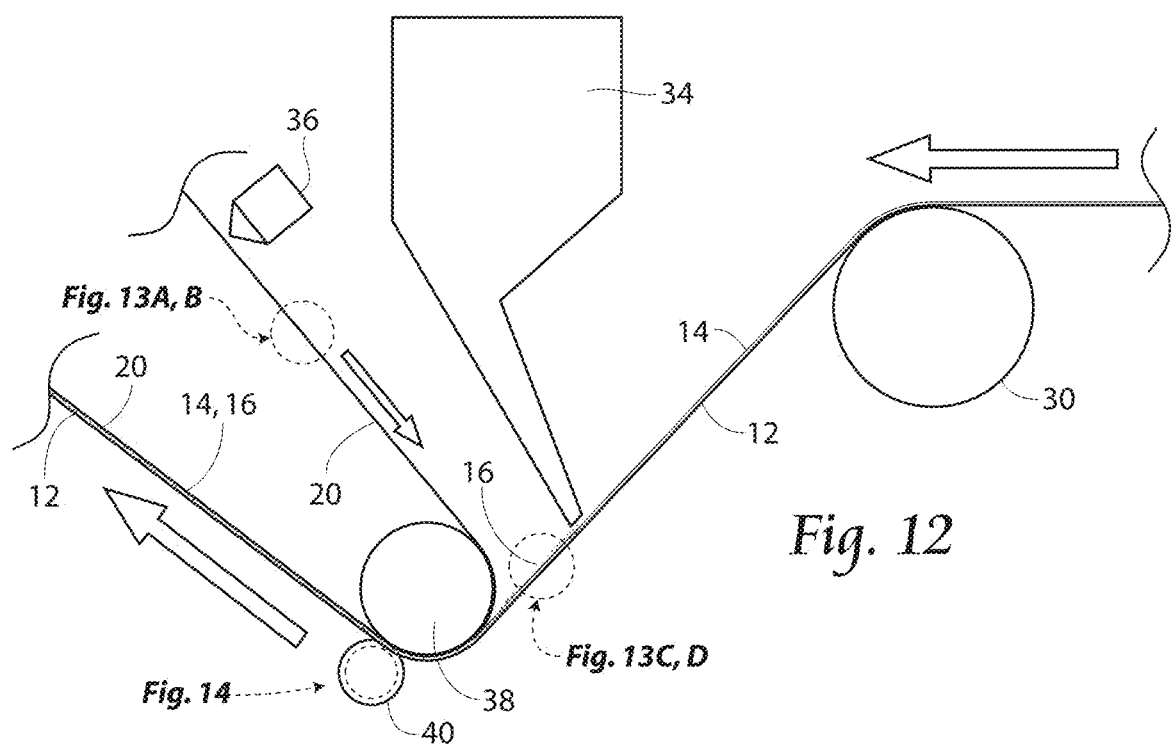
FIG. 12 is a side view of other portions of the system for producing an absorbent core shown in FIG. 10.

Referring now to FIG. 12, after the elastic 14 is coupled to the base nonwoven 12, base nonwoven 12 is preferably slightly de-tensioned between roller 30 and roller 38/nip 40 combination to accommodate receipt of SAP 16 by the base nonwoven 12 by creating a slight furrow for SAP 16.

Draw ratios of elastic 14 can be varied. A larger draw ratio could reduce SAP 16 level per unit of nonwoven 12/elastic 14, but when relaxed, the SAP 16 can be contained in a relatively small area to achieve a high effective concentration of SAP. On the other hand, a smaller draw ratio will increase SAP level per unit of nonwoven 12/elastic 14. In this case, a higher SAP doping rate is used to achieve a high effective concentration of SAP. Higher draw ratio may desirably give a softer feel to the composite and when lower draw ratio can also reduce the cost of manufacturing. By changing the draw ratio, the performance and cost balance can be easily adjusted.

A SAP distribution system 34 applies SAP 16 to the base nonwoven 12. Incoming top nonwoven layer 20 receives adhesive from adhesive distribution system 36, and top nonwoven layer 20 is brought into contact with the base nonwoven 12 and elastic strand 14 combination at roller 38/nip 40 combination to create an absorbent core laminate 12/14/16/20 which is passed downstream for further processing as desired, for example cutting/placing, stacking, or rolling.

Figure 13A:
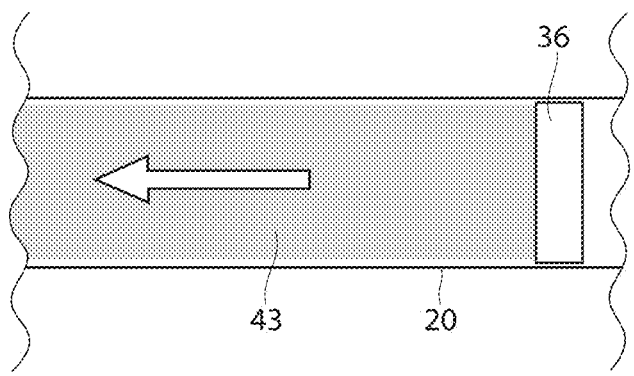
FIG. 13A is bottom view of a system for applying adhesive to a top nonwoven layer for use in creating an absorbent core.
Figure 13B:
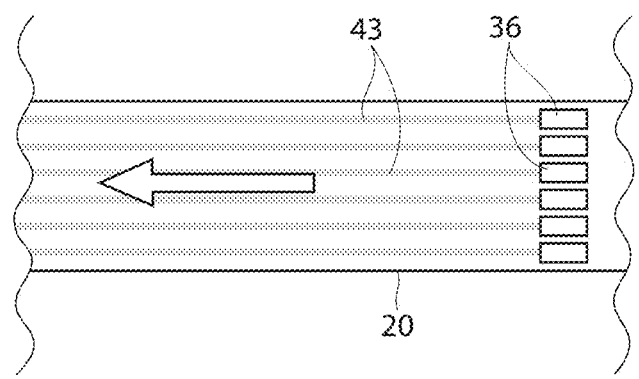
FIG. 13B is a bottom view of an alternate system for applying adhesive to a top nonwoven layer for use in creating an absorbent core.

Referring now to FIG. 13A, a bottom view of adhesive applicator 36 is shown, applying adhesive 43 in a pattern to the bottom of top nonwoven layer 20. As shown in FIG. 13A, the pattern can be substantially continuous across desired areas of top nonwoven layer 20, or as shown in FIG. 13B, adhesive 43 can be applied in a striped pattern to top nonwoven 20. It may be desirable to apply adhesive 43 in a striped pattern to correlate to the spacing of elastic strands 14 carried by base nonwoven 12. As the spacing and orientation of elastic strands 14 carried by base nonwoven 12 can vary in spacing, orientation and laydown pattern, so too can the pattern of adhesive 43 applied to top nonwoven 20.

Figure 13C:
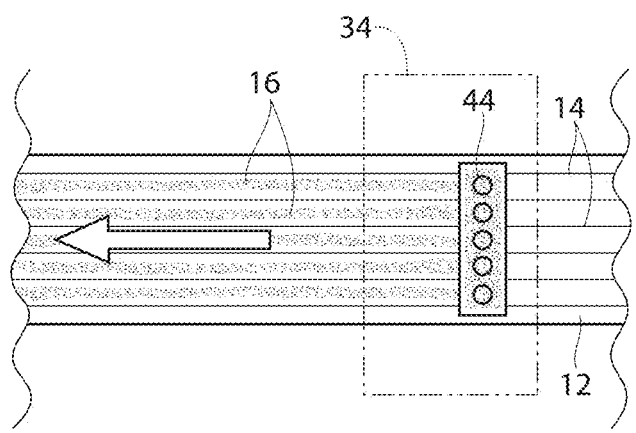
FIG. 13C is a top view of a SAP distribution system applying SAP in a preferred embodiment of SAP lanes to a base nonwoven layer coupled to elastic strands.
Figure 13D:
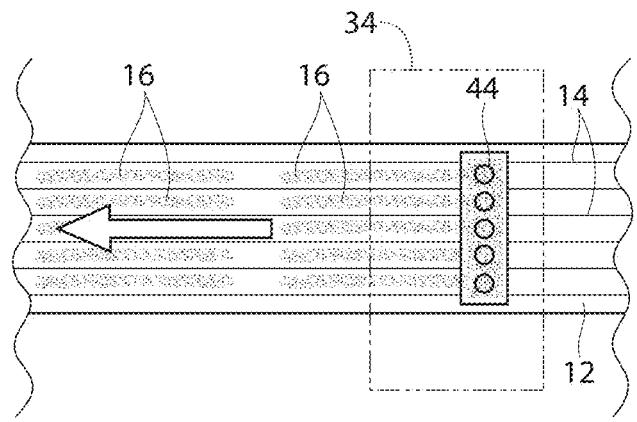
FIG. 13D is a top view of a SAP distribution system applying SAP in a second preferred embodiment of intermittent SAP lanes to a base nonwoven layer coupled to elastic strands.

Referring now to FIG. 13C, a top view of a SAP distribution system 34 applying SAP 16 in a preferred embodiment of SAP 16 lanes to a base nonwoven layer 72 coupled to elastic strands 14 is shown. SAP 16 is received from a source such as a fed hopper as shown in FIG. 12, and passed to void spaces 44 in the SAP distribution system 34 to allow SAP 16 to be applied to the base nonwoven 12. A preferred SAP 16 laydown pattern is lanes or stripes as depicted in FIG. 13C, and as shown in FIG. 13D, these lanes can be intermittent SAP 16 lanes. Intermittent SAP 16 distribution is accomplished for example by interrupting the inbound flow of SAP 16, or by removing intermittently portions of the flow of SAP 16.

By forming puckers, channels or lanes in the core with SAP 16, retention, acquisition and distribution of liquid is assisted. In an alternative embodiment, alternating patterns or divergent patters of channels or lanes of SAP can be created by heavy and light SAP 16 distribution levels. This also enhances the distribution performance of the core and allows for the performance to be tailored according to the desired usage. In this manner, elastic strand 14 spacing can be alternated with heavy SAP 16 lanes adjacent to light SAP 16 lanes that can channel the liquid in a desired pattern.

The present invention allows for use of a thinner ADL layer because the contracted core is corrugated and can store liquid. The ADL layer can be allowed to contract with the absorbent core laminate 12/14/16/20 and the result is a fully elastic core in zones where elastification is desired.

For a higher dosage of SAP 16, larger (or longer) void spaces 44 and feed rate can be used. Likewise, for a lower dosage of SAP 16, smaller void spaces 44 and feed rates can be used.

Figure 14:
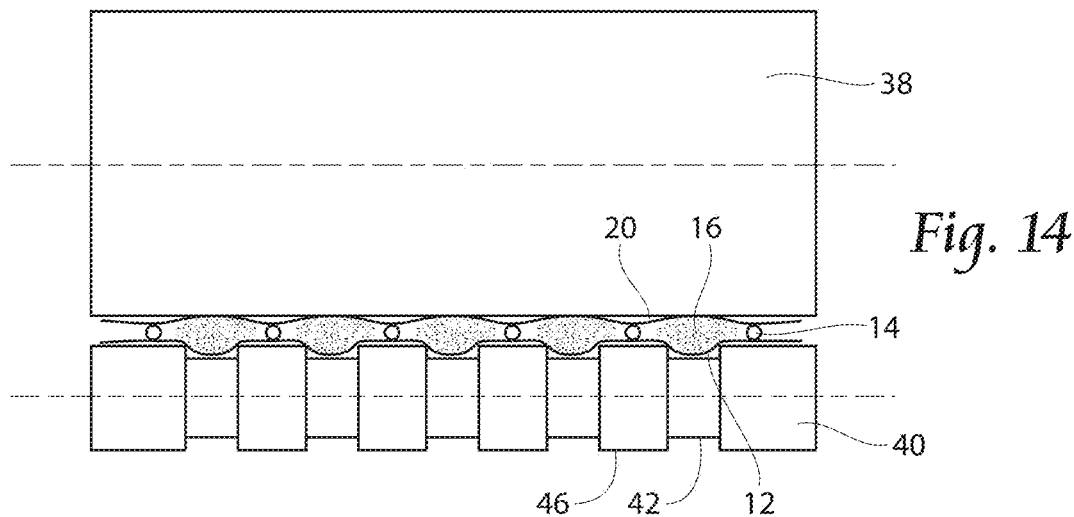
FIG. 14 is a side view of a roller/nip combination coupling a top nonwoven layer to elastic strands carried by a base nonwoven layer, the base nonwoven layer carrying SAP material.
Figure 15:
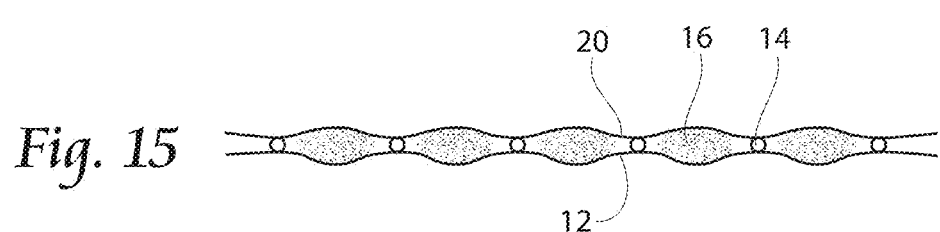
FIG. 15 is a cross sectional view of a top nonwoven layer coupled to elastic strands carried by a base nonwoven layer, the base nonwoven layer carrying SAP material to form an absorbent core laminate.
Figure 18:
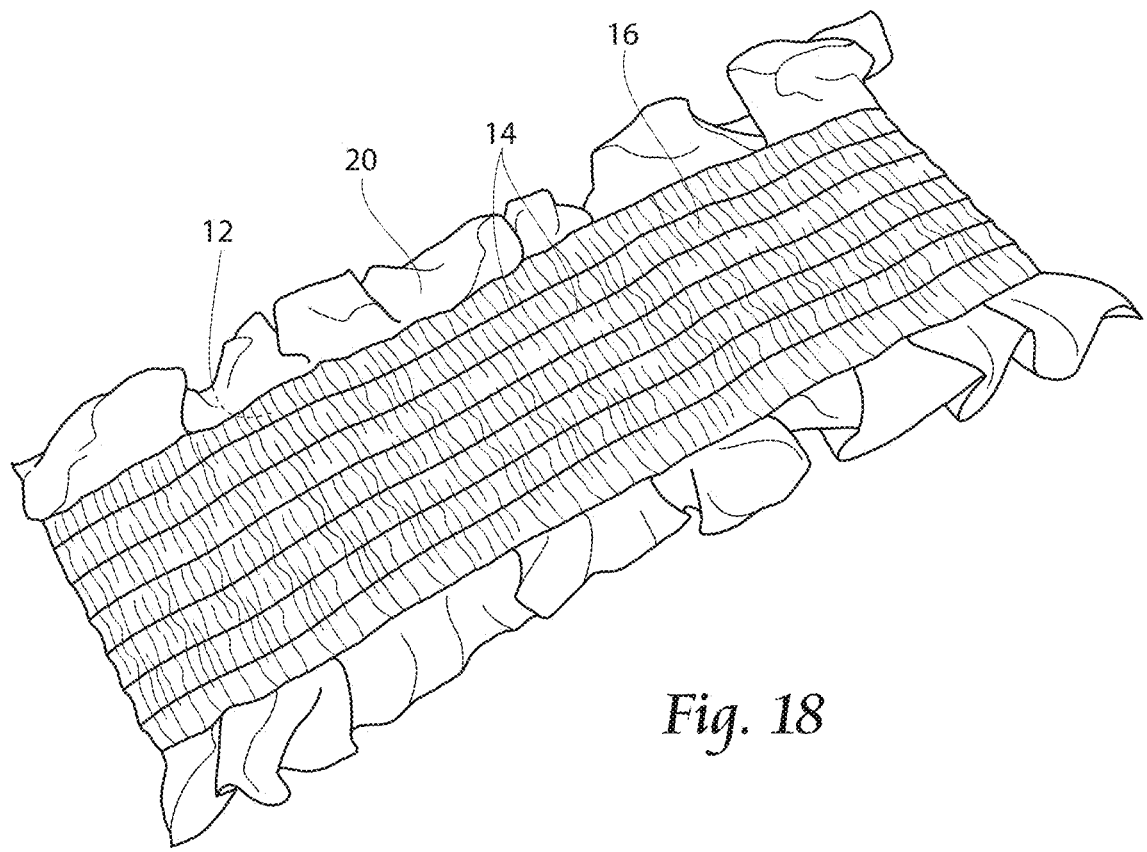
FIG. 18 is a perspective view of an absorbent core laminate.

Referring now to FIG. 14, once SAP 16 has been applied to the base nonwoven layer 12, and adhesive 43 has been applied in a pattern to the bottom of top nonwoven layer 20, the materials of the absorbent core laminate 12/14/16/20 are brought together by nip wheel 38 urging the top nonwoven 20 carrying adhesive 43 against elastic strands 14. Base nonwoven 12 is carried by ridged nip wheel 40. In a preferred embodiment, peaks 46 of the ridged nip wheel 40 carry base nonwoven 12 and elastic strands 14, and the elastic strands 14 carried by base nonwoven 12 are urged into contact with top nonwoven 20. Valleys 42 of the ridged nip wheel 40 allow SAP 16 a position to migrate during compression of the materials of the absorbent core laminate 12/14/16/20 and coupling of the top nonwoven 20 to elastic strands 14. SAP 16 accumulates in the valleys 42. As shown in FIG. 15, an absorbent core laminate 12/14/16/20 is formed, with SAP 16 remaining captured in pockets, to create an absorbent core laminate 12/14/16/20 as shown in FIG. 18.

Figure 16:
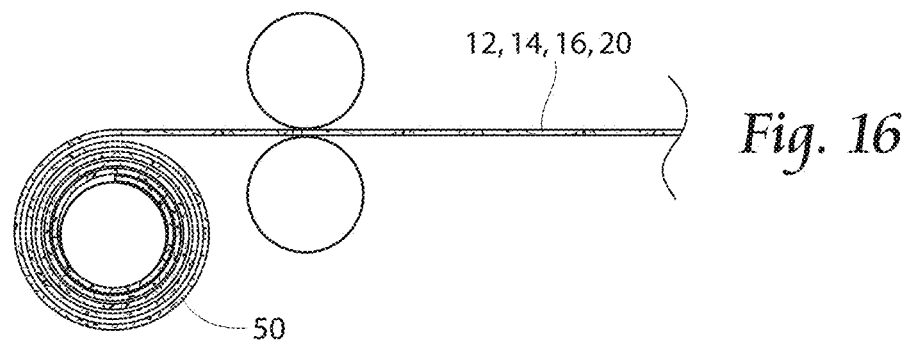
FIG. 16 is a side view of a system for winding a top nonwoven layer coupled to elastic strands carried by a base nonwoven layer, the base nonwoven layer carrying SAP material to form an absorbent core laminate.
Figure 17:
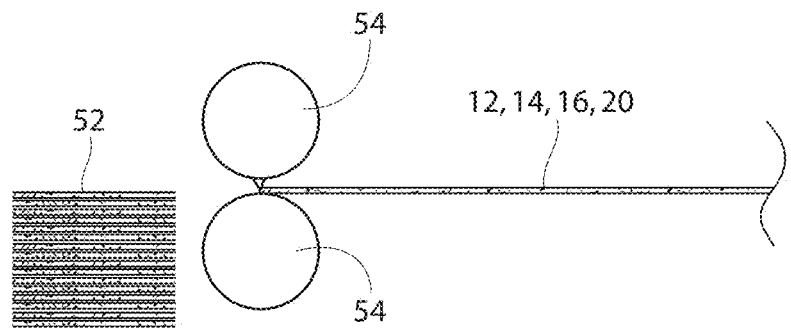
FIG. 17 is a side view of a system for stacking a top nonwoven layer coupled to elastic strands carried by a base nonwoven layer, the base nonwoven layer carrying SAP material to form an absorbent core laminate.

After creation of the absorbent core laminate 12/14/16/20, laminate is passed downstream for further processing as desired. This can include winding to create a roll 50 of absorbent core laminate 12/14/16/20 as shown in FIG. 16, cutting and stacking of absorbent core laminate 12/14/16/20 as shown in FIG. 17. Referring to FIG. 17 in particular, is a side view of a system for stacking a top nonwoven layer coupled to elastic strands carried by a base nonwoven layer, the base nonwoven layer carrying SAP material to form an absorbent core laminate is shown. A stack 52 of discrete absorbent core laminate 12/14/16/20 pieces can be assembled for packaging.

Preferably, absorbent core laminate 12/14/16/20 is cut and placed, and this cutting and placing can take any fashion such as traditional cores are variably placed in disposable product construction. For instance, the formed absorbent core laminate 12/14/16/20 can be situated adjacent to an acquisition/distribution (ADL) layer (not shown).

Figure 19:
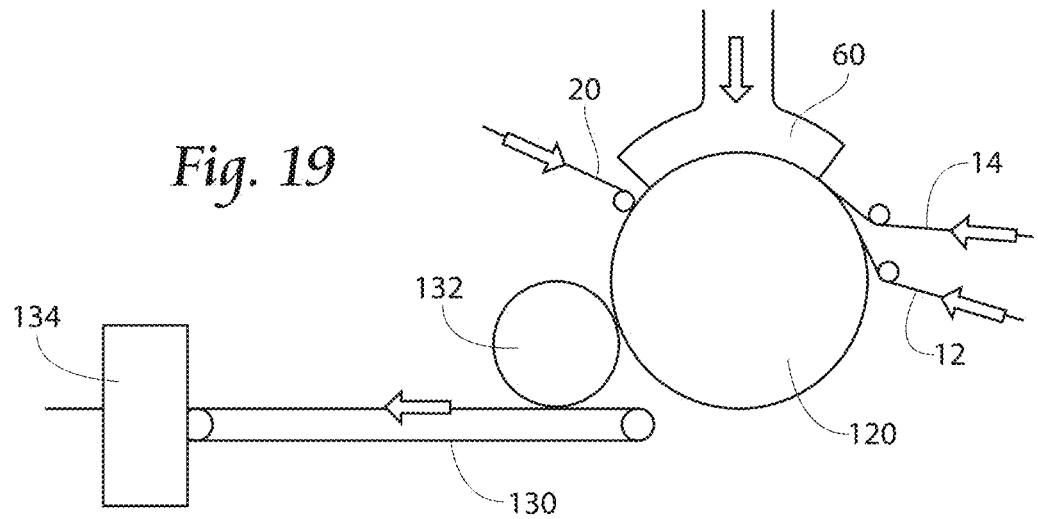
FIG. 19 is a side schematic view of a process of the present invention for forming a tubular absorbent product of the present invention.
Figure 20:
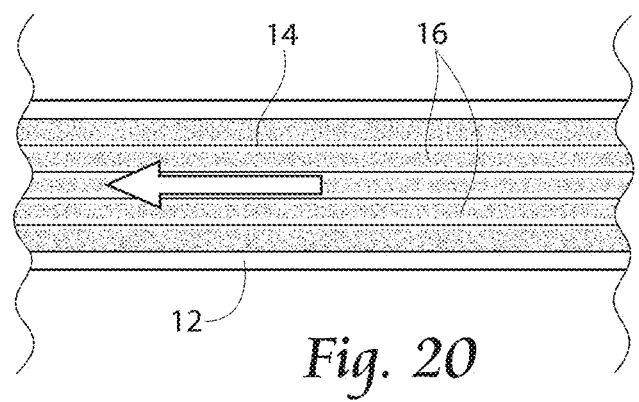
FIG. 20 is a top view of a continuous tubular core formation produced with a machine according to FIG. 19.

Referring now to FIG. 19, a side schematic view of a process of the present invention for forming a tubular absorbent product of the present invention is shown. A lower nonwoven web 12 is fed onto forming drum 120. Fed atop lower nonwoven 12 is elastic 14, preferably stranded. And absorbent material distribution unit 60 feeds absorbent material 16 onto lower nonwoven 12, and top nonwoven 20 covers the absorbent material 16 fed from absorbent material distribution unit 60. Turning drum 132 feeds the laminate onto conveyor 130, turning drum 132 [1] receives the composite web from the forming drum 120 and [2] transfers the composite web to the conveyor 130, where the composite web 12/14/16/20 is presented to core knife 134, and fed downstream for further processing as necessary. One possible result is shown in FIG. 20, a top view of a continuous tubular core formation.

Figure 19A:
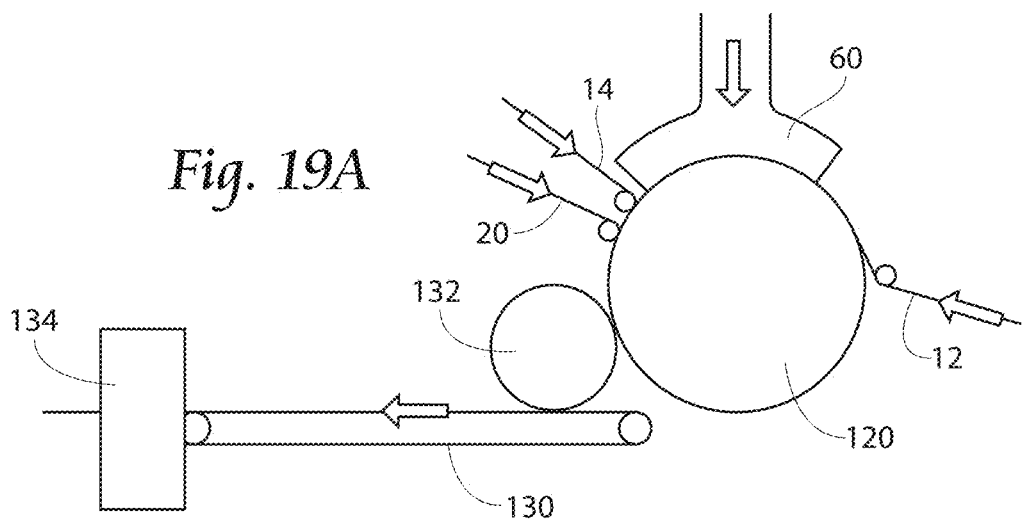
FIG. 19A is a side schematic view of an alternate process of the present invention for forming a tubular absorbent product of the present invention.

Referring now to FIG. 19A, a side schematic view of an alternate process of the present invention for forming a tubular absorbent product of the present invention is shown. In this embodiment, elastics 14 are introduced downstream of absorbent material 16 being fed from absorbent material distribution unit 60, and then top nonwoven 20 is provided to cover the absorbent material 16 and elastic strands 14. In this embodiment, the elastic 14 does not rotate through the forming chamber 60, and this may be advantageous to avoid elastic fouling any scarf combing operations (not shown) where any fluff or SAP collects.

Figure 21:
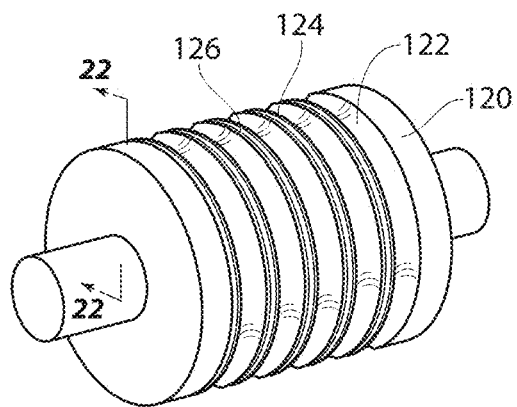
FIG. 21 is a perspective view of a forming drum for forming a tubular core, with tube forming pockets which can be profiled to match tube zones, and a raised profile with a channel for receiving elastic placements.

Referring now to FIG. 21, a perspective view of a forming drum 120 for forming a tubular core of absorbent is shown. Tube forming pockets or channels 122 can be profiled to match tube zones (e.g., rectangular, ovular), and a raised profile 124 divides adjacent forming pockets 122. In a preferred embodiment, a channel 126 configured for receiving elastic placements (the elastic 14 shown in FIGS. 19 and 20, for instance) can be provided preferably atop the raised profiles 124.

Figure 22:
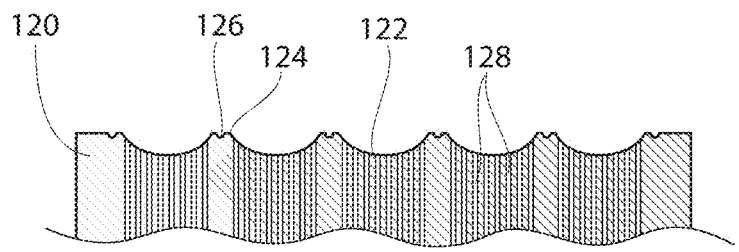
FIG. 22 is a cross-sectional view of the forming drum of FIG. 21, showing tube forming pockets which can be profiled to match tube zones, and a raised profile with a channel for receiving elastic placements, and vacuum commutation ports for assisting tubular core formation.

FIG. 22 is a cross-sectional view of the forming drum 120 of FIG. 21, showing tube forming pockets 122 which can be profiled to match tube zones, and a raised profile 124 with a channel 126 for receiving elastic 14 placements, and vacuum commutation ports 128 for assisting tubular core formation. Vacuum commutation ports 128 can be provided in the interior of forming drum 120, for urging transported absorbent material 16 towards the surface of forming pockets 122. Vacuum commutation ports 128 can be provided with vacuum (for instance at a sidewall of rotating forming drum 120, not shown) in a manner known in the art, for instance as disclosed in U.S. Pat. No. 7,533,709, disclosed herein by reference.

Figure 23:
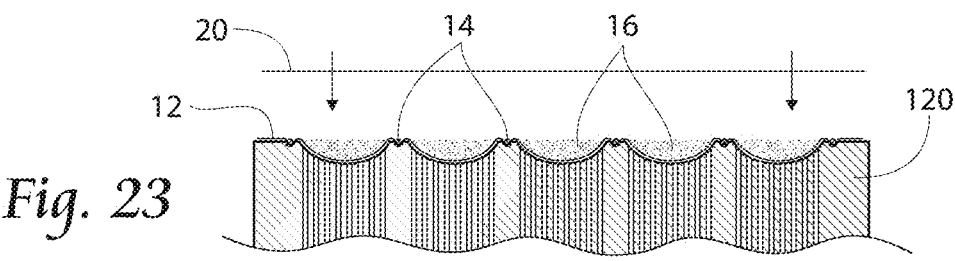
FIG. 23 is a side cross-sectional view of forming drum of FIG. 22, carrying a sheet of non-woven material placed into tube forming pockets, filled with absorbent material, and a raised profile with a channel that received elastic placements, and a waiting non-woven sheet to be placed to top a laminate formed thereby.
Figure 24:
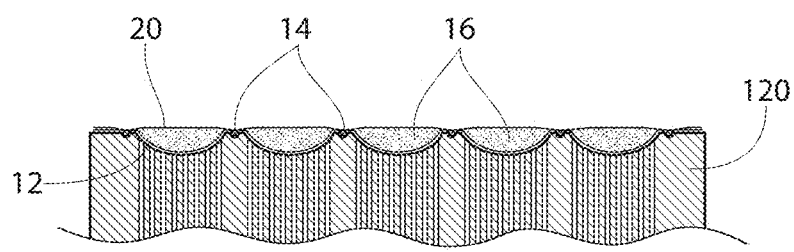
FIG. 24 is a cross-sectional view of the laminate formed in FIG. 23.

In use, as shown in FIG. 23, a sheet 12, preferably of nonwoven material, is introduced onto forming drum 120 (see also, FIG. 19). Absorbent material 16 (e.g., SAP material, fluff material, or a SAP/fluff mixture) is laid down, as well as elastic strands 14. Preferably the absorbent material 16 fills but does not overfill tube forming pockets or channels 122. A waiting non-woven sheet 20 is placed atop a laminate formed thereby, and the laminate formation is completed as shown in FIG. 24 by bonding the topsheet 20 to the backsheet 12 preferably at raised profile areas 124 between adjacent channels 122 or to their side in the case of the side of the product. It is preferred that the bonding of the topsheet 20 to the backsheet 12 take place in areas without interfering strands 14 or absorbent material 16. The technique of laying down a web 12 atop vacuum commutation ports 128 can be referred to as form-on non-woven, and the elastics 14 and the top non-woven 20 are combined to form a continuous composite web 12/16/14/20, of discrete formed core tubes.

Figure 25:
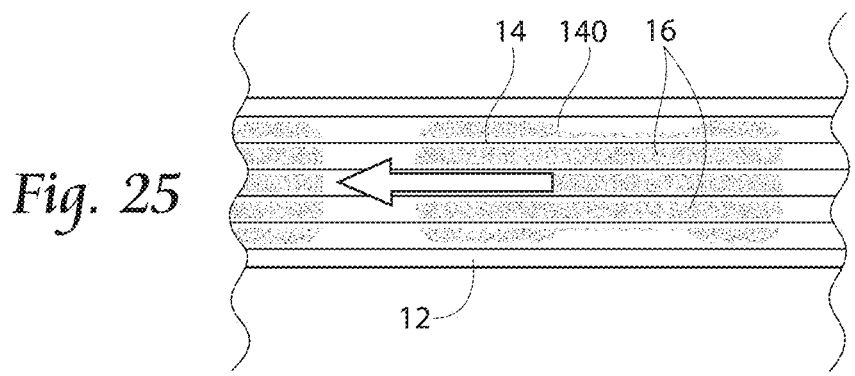
FIG. 25 is a top plan view of discrete tubular absorbent core formation.
Figure 26:
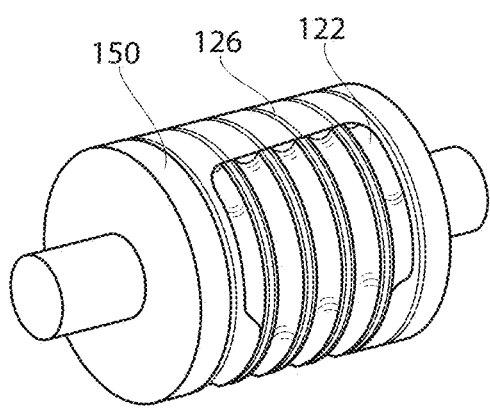
FIG. 26 is a perspective view of an apparatus for forming discrete tubular absorbent cores.

Referring now to FIG. 25, if discrete tubular absorbent cores 140 (as opposed to the continuous channels of FIG. 20), forming drum 120 can be modified as shown in FIG. 26 by including core blocking areas around the perimeter of the drum 120, to block introduction of absorbent material 16 into channels 122.

Figure 27:
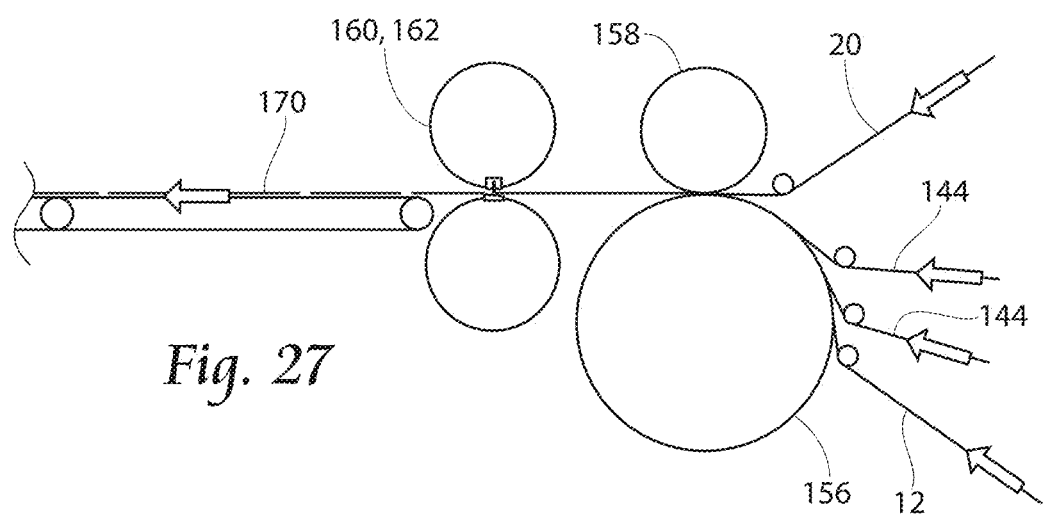
FIG. 27 is a side schematic view of an apparatus for forming discrete cores from a continuous process.
Figure 28:
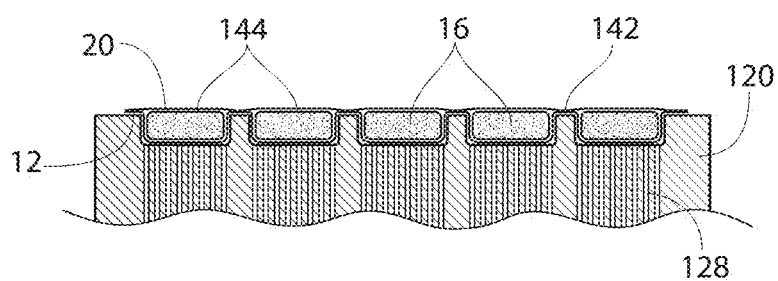
FIG. 28 is a side cross-sectional view of an alternate embodiment to the forming drum of FIG. 23, the embodiment shown in FIG. 28 creating rectangular tubes adjacent to one another.
Figure 29:
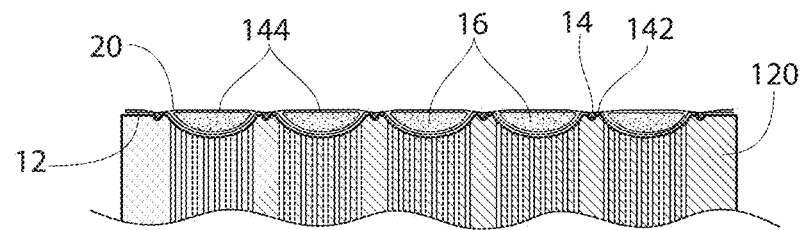
FIG. 29 is a side cross-sectional view of a forming drum during an alternate embodiment of the tubular core formation.

Referring now to FIG. 27, an alternate technique is shown for creating tubular cores. A first carrier web layer 12 is introduced to forming drum 156, and bonding drum 158. Next, pre-formed individual core strips 144 which can be formed or made independently from each other, are introduced atop the carrier web layer 12. The introduced core elements 144 could be formed upstream on separate forming drums, and wrapped, and then the individual wrapped core elements 144 could be combined between the lower 12 and upper cover web layers 12 and 20 respectively, which are then be bonded to one another to form web to web bonds 184 between the tubular core elements 144. This creates continuous channels of void space between adjacent tubular absorbent members 144, for instance a rectangular or tubular formation as shown in FIG. 28, and an ovular tubular core shown in FIG. 29. An anvil/knife combo 160/162 can next sever the absorbent cores into discrete core units 170 and pass those downstream.

Figure 30:
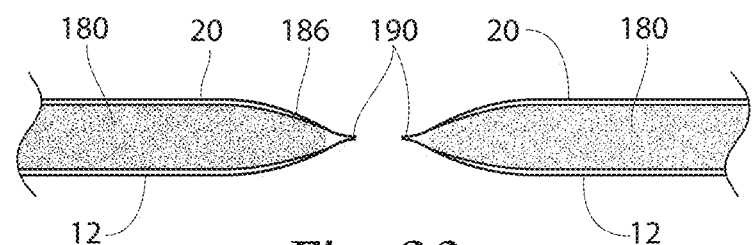
FIG. 30 is a side view of a wrapped core.
Figure 31:
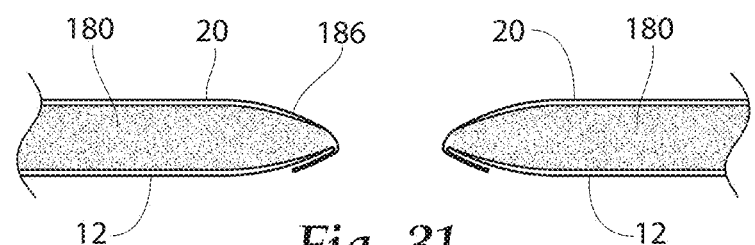
FIG. 31 is an alternate embodiment of a side seaming technique for a wrapped core.

In one embodiment, vertical form fill seal machines (not shown in the figures, one example described in U.S. Pat. No. 6,182,426 incorporated herein by reference) can be used to create individual lanes 186 of absorbent material such as shown in FIG. 30. A source of absorbent material 180 is fed by gravity vertically into a series of tubular nonwoven 12 and 20 wraps. The individual lanes or tubes 186 can be fed downstream and sealed at end seals 190 at appropriate intervals to create individually wrapped (almost teabag appearing) core elements 186. Examples of wrapped cores are shown in FIGS. 30 and 31, and it is these types of individual core strips 186 which could be introduced atop carrier web layer 12 and combined with carrier web 20 to achieve the product shown in FIG. 32.

Figure 32:
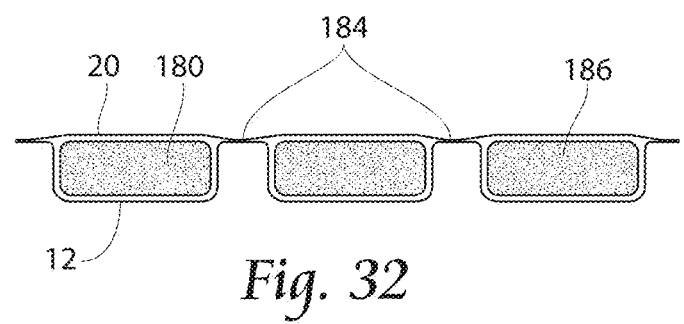
FIG. 32 is a side cross-sectional view of tubular cores of the present invention.

Referring still to FIG. 32, an alternative embodiment is shown. Separate core elements 180 (wrapped in nonwoven 12/20) are created in preferred embodiments either vertically (described above) or on separate forming drums (not shown), and then the individual wrapped core elements 180 are encapsulated between two additional nonwoven webs 12/20. In a preferred embodiment, the exterior webs 12/20 are bonded together at bond points 184 to form web-to-web bonds 184 between the core elements 180. This creates continuous void channels (preferably free of fluff and/or SAP) near bond points 184 between core elements 186. Core elements 186 could be preferably continuous, or discrete (like elongated pillows).

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A method of forming a disposable product comprising: providing a base layer; providing a series of tubular absorbent core members of absorbent material carried by said base layer; forming said tubular absorbent core members on a rotating vacuum drum such that said tubular absorbent core members are adjacent to each other, said rotating vacuum drum having adjacent pockets shaped to carry a predetermined amount of said absorbent material; providing a topsheet; providing an elastic strand carried between said base layer and said topsheet, said elastic strand laid down within a channel formed on a raised profile positioned between said adjacent pockets on the rotating vacuum drum, such that said elastic strand is provided between said adjacent tubular absorbent core members; and coupling said topsheet to said base layer between said adjacent tubular absorbent core members of said series of tubular absorbent core members to create a continuous composite web of absorbent core material.

2. A method according to claim 1, the method further comprising providing said tubular absorbent core members parallel to one another.

3. A method according to claim 1, wherein said absorbent material comprises at least one of superabsorbent polymer or fluff material.

4. A method according to claim 1, the method further comprising forming said tubular core members with a nonwoven wrap encapsulating said absorbent material, prior to said step of providing said series of tubular absorbent core members of said absorbent material carried by said base layer.

5. A method according to claim 4, the method further comprising end sealing said tubular core members in a machine direction at a first and a second end of said tubular core members.

6. A method according to claim 1, the method further comprising continuously bonding said base layer and said top layer between said adjacent tubular core members.

7. A method according to claim 1, the method further comprising intermittently bonding said base layer and said top layer between said adjacent tubular core members.

8. A method according to claim 1, the method further comprising severing said continuous composite web into discrete cores.

9. A method according to claim 1, further comprising providing core blocking areas around a perimeter of said rotating vacuum drum to block introduction of said absorbent material into portions of said pockets.

* * * * *